(12) United States Patent
Liu et al.

(10) Patent No.: US 8,753,673 B2
(45) Date of Patent: Jun. 17, 2014

(54) LIPOSOME COMPOSITION FOR DELIVERY OF A THERAPEUTIC AGENT TO EYES

(75) Inventors: Jun-Jen Liu, Taipei (TW); Chi-Chun Lai, Taipei (TW); Yun-Long Tseng, Taipei (TW); Luke S. S. Guo, South San Francisco, CA (US); Keelung Hong, South San Francisco, CA (US)

(73) Assignees: Taiwan Liposome Co. Ltd., Nankang, Taipei (TW); TLC Biopharmaceuticals, Inc., South San Francisco, CA (US)

( * ) Notice: Subject to any disclaimer, the term of this patent is extended or adjusted under 35 U.S.C. 154(b) by 1093 days.

(21) Appl. No.: 11/419,825

(22) Filed: May 23, 2006

(65) Prior Publication Data

US 2007/0275048 A1 Nov. 29, 2007

(51) Int. Cl.
*A61K 39/395* (2006.01)
*A61K 31/724* (2006.01)
*A61K 31/555* (2006.01)
*A61K 9/127* (2006.01)

(52) U.S. Cl.
USPC .............. 424/450; 977/907; 514/184; 514/58

(58) Field of Classification Search
None
See application file for complete search history.

(56) References Cited

U.S. PATENT DOCUMENTS

| 6,110,491 | A * | 8/2000 | Kirpotin | 424/450 |
| 2004/0018230 | A1 * | 1/2004 | Grant et al. | 424/450 |
| 2004/0219204 | A1 * | 11/2004 | Huang et al. | 424/450 |

FOREIGN PATENT DOCUMENTS

WO    WO 0174389 A2 * 10/2001

OTHER PUBLICATIONS

T Otsuji, N Ogata, K Takahashi, M Matsushima, M Uyama, Y Kaneda. "In vivo gene transfer into choroidal neovascularization by the HVJ liposome method." Graefe's Arch Clin Exp Ophthalmol (2000) 238, pp. 191-199.*
F Carey. "Chapter 22: Amines." (http://www.chem.ucalgary.ca/courses/351/Carey/Ch22/ch22-1.html) pp. 1-4, May 19, 2001, as of Internet Archive.*
Jo Thomas. "HMG1 and 2: architectural DNA-binding proteins." Biochemical Society Transactions (2001) vol. 29, part 4, pp. 395-401.*
E Sakurai, H Ozeki, N. Kunou, Y Ogura. "Effect of Particle Size of Polymeric Nanospheres on Intravitreal Kinetics." Ophthalmic Research, 2001, vol. 33, pp. 31-36.*
S Farrell, KK Sirkar. "Controlled Release of Liposomes." Journal of Membrane Science, vol. 127, 1997, pp. 223-227.*
Taiwan Search Report, received Mar. 12, 2009, one page.
Awasthi, V.D. et al., "Circulation and biodistribution profiles of long-circulating PEG-liposomes of various sizes in rabbits," International Journal of Pharmaceutics, 253 (2003), pp. 121-132.

* cited by examiner

*Primary Examiner* — Frederick Krass
*Assistant Examiner* — Celeste A Roney
(74) *Attorney, Agent, or Firm* — Husch Blackwell LLP; Robert M. Gould (57) ABSTRACT

The invention provides a liposome composition for delivering high pay-load of a therapeutic agent to neovascularization sites of the eyes in a patient in need thereof. The liposome composition for entrapping the therapeutic agent comprises a particle forming component composed of a variety of vesicle-forming lipids, and an agent-carrying component able to form a complex with the therapeutic agent via electrostatic charge-charge interaction or hydrophobic-hydrophobic interaction; wherein the liposome composition comprising the therapeutic agent has a mean particle diameter of about 30 to 200 nm and may accumulate at the neovascularization sites of the eyes 24 hours after the intravenous administration of the liposome composition comprising the therapeutic agent to the patient. A method for delivering the therapeutic agent to the eyes in a patient with this liposome composition is also provided.

14 Claims, 4 Drawing Sheets

Fig. 1

A. Normal (left) eye    B. CNV (right) eye

LIPOSOME COMPOSITION FOR DELIVERY OF A THERAPEUTIC AGENT TO EYES

BACKGROUND OF THE INVENTION

The present invention is generally related to a drug delivery, and more particularly related to a liposome composition for delivery of a therapeutic agent to eyes in patients.

Eye diseases, such as age-related macular degeneration (AMD) and diabetic retinopathy (DR) that occur at the back of eyes are the leading causes of blindness in the elderly and many productive individuals in the developed country (Aiello, L. M. (2003) *Am. J. Ophthalmol.* 136, 122-135; Klein, R. et al. (1992) *Ophthalmology* 99, 933-943). Neovascularization or formation of new blood vessels, in retinal or choroidal tissues is a central feature of these diseases. This pathological angiogenesis causes visual loss through increased vascular permeability leading to retinal edema, vascular fragility resulting in intraocular hemorrhage, or fibrovascular proliferation with tractional and rhegmatogenous retinal detachment (Ferris, F. L. et al. (1984) *Arch Ophthalmol.* 102, 1640-1642; Archer, D. B. (1999) *Eye* 13, 497-523). The current accepted treatments for these diseases including thermal laser photocoagulation and photodynamic therapy provided clinical benefits but are associated with significant adverse effects (Early Treatment Diabetic Retinopathy Study Research Group (1991) *Ophthalmology* 98, 766-785; Ciulla, T. A. et al. (1998) *Surv. Ophthalmol.* 43, 134-146; Verteporfin In Photodynamic Therapy Study Group (2001) *Am. J Ophthalmol.* 131, 541-560). Moreover, these treatments are associated with high rates of persistent and recurrent disease accompanied by an increased frequency of severe visual loss (Macular Photocoagulation Study Group (1986) *Arch. Ophthalmol.* 104, 503-512; Macular Photocoagulation Study Group (1994) *Arch. Ophthalmol.* 112, 489-499). A large number of new therapies have focused on pharmacological agents that inhibit the process of angiogenesis (Das, A. et al. (2003) *Retinal and Eye Research* 22, 721-748). For an effective therapy, it is essential that a therapeutic concentration of the pharmacological agent to be present at the disease site for an extended period of time.

Eye is an enclosed organ of the body. The blood circulation through the eye is slower than the rest of the body. Delivery of an effective dose of the drug to the eye, particularly the rear end of the eye, such as retinal or choroidal tissues, remains a difficult task. Current methods for ocular drug delivery include topical administration (eye drops), systemic administration (oral or intravenous), subconjunctival injection, periocular injection, intravitreal injection, and surgical implant. However, all these methods have limitations in delivering drugs to the back of the eye. The tissues of the lens, sclera, vitreous, etc. prevent drugs from readily moving from the front of the eye to the back when the topical eye drops are used. The systemic route of drug delivery following oral or intravenous administration has limitations as the drug may not reach the target tissues at an optimal concentration without the risk of systemic toxicities. Intravitreal injections, periocular injections, and sustained-release implants can be used to achieve therapeutic levels of drugs in ocular tissues, but invasive methods are inherently risky due to the potential for bleeding, infection, retinal detachment, and other local injuries.

Liposome and lipid/drug complex have been widely studied and employed as vehicles for intravenous administration of therapeutic agents. Liposome is a spherical, self-enclosed vesicle composed of amphipathic lipids. Therapeutic agents can be encapsulated in the aqueous compartment or intercalated into the lipid bilayer of the vesicle (Szoka, F. Jr. and Papahadjopoulos, D. (1980) *Ann. Rev. Biophys. Bioeng.* 9, 467-508). The lipid/drug complex, on the other hand, is formed by hydrophobic-hydrophobic or/and electrostatic charge-charge interactions between the lipids and drugs, such as lipid : amphotericin B complexes (Janoff, A. S. et al. (1988) *Proc. Natl. Acad. Sci. USA.* 85, 6122-6126; Guo, L. S. S. et al. (1991) *In. J. Pharm.* 75, 45-54) and lipid : nucleic acid complexes described in U.S. Pat. Nos. 6,071,533 and 6,210,707 B1. Studies have shown that these micro-or nano-particles can decrease the toxicity and enhance the efficacy of several anticancer and antifungal drugs (Gabizon, A. A. (1992) *Cancer Res.* 52, 891-896; Northfelt, D. W. et al. (1998) *J. Clin. Oncol.* 16, 2445-2451; Oppenheim, B. A. et al. (1995) *Clin. Infect. Dis.* 21, 1145-1153). In particular, the so-called long circulating liposome includes a surface coat of soluble polymer chains, which act to prevent in vivo uptake by mononuclear phagocytic system (Allen, T. M. et al. (1991) *Biochim. Biophys. Acta* 1066, 29-36; Chonn, A. et al. (1992) *J. Biol. Biochem.* 267, 18759-18765; U.S. Pat. No. 5,013,556). The therapeutic benefit associated with the long-circulating liposomes is believed to relate to increase delivery of drug in disease tissues such as tumors (Papahadjopoulos, D. et al. (1991) *Proc. Natl. Acad. Sci. USA.* 88, 11460-11464; U.S. Pat. No. 5,213,804) and sites of infection (Bakker-Woudenberg, IAJM et al. (1993) *J. Infect. Dis.* 168, 164-171; U.S. Pat. No. 5,356,633) and inflammation (Rosenecker, J. et al. (1996) *Proc. Natl. Acad. Sci. USA.* 93, 7236-7241; U.S. Pat. No. 5,843,473).

Figure 1:
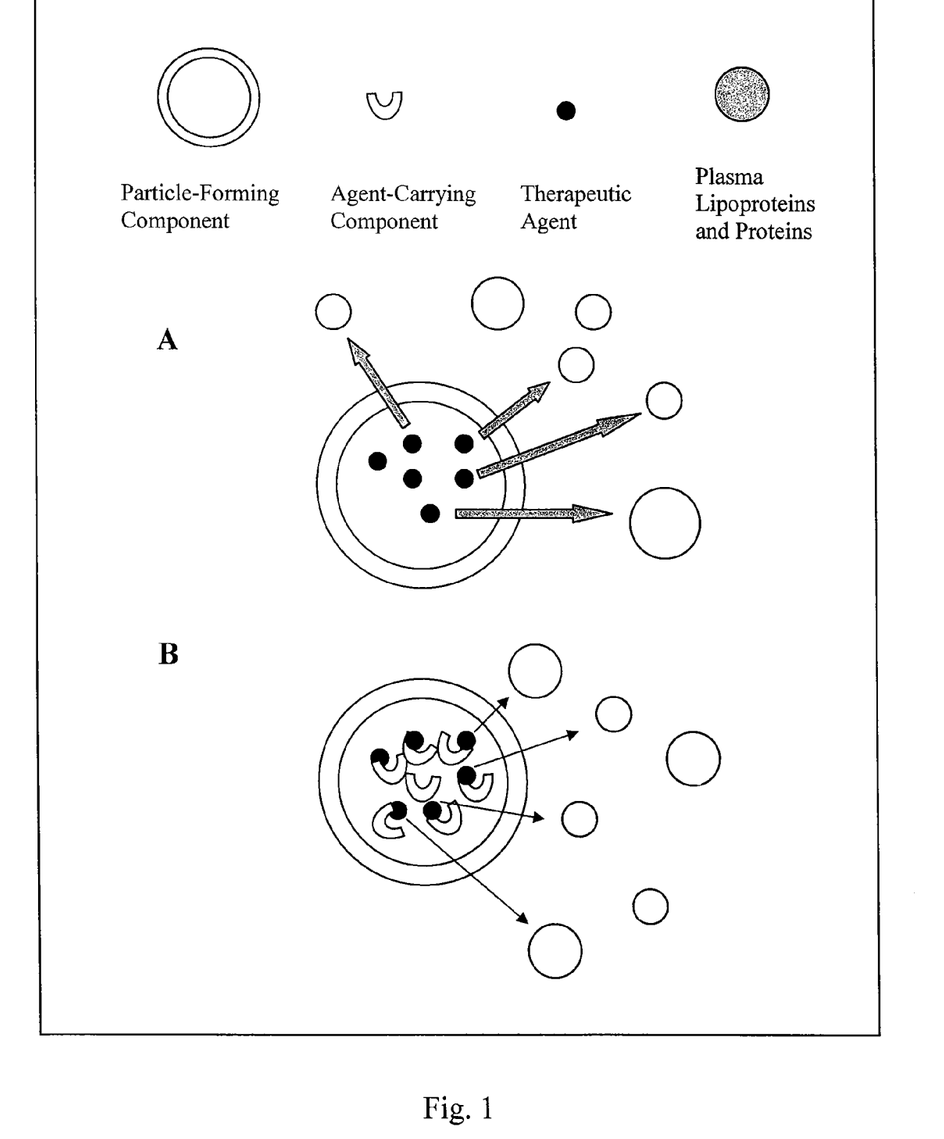
FIG. 1A is a schematic diagram illustrating a conventional liposome particle having therapeutic agent entrapped within a particle forming component.
FIG. 1B is a schematic diagram illustrating a liposome particle having both the therapeutic agent and agent-carrying component entrapped within a particle forming component according to one preferred embodiment of the invention.

Several methods/systems have been disclosed for delivering material encapsulated in liposome to the eye through the blood stream. U.S. Pat. No. 4,891,041 describes a method of selectively and repetitively releasing a material at a specific site in the blood stream inside the body of an animal, including the eye. The method uses a heat-sensitive lipid vesicle comprising a specific lipid composition. Following injecting the lipid vesicles into the blood stream, a laser beam is applied to trigger the release of the encapsulated material at the specific site of the tissue. U.S. Pat. No. 6,074,666 and US 2003/0087889 disclosed a liposome composition of porphyrin photosensitizers for photodynamic therapy in treating occult choroidal neovascular lesions in AMD patients. The liposomal photosensitizer is given by intravenous injection and followed by applying laser light to the eye to sensitize the photosensitizer. However, as shown in FIG. 1 A, most of the administered hydrophobic porphyrin compound separates from the liposome in the blood stream and incorporates into plasma lipoproteins which subsequently serve as an endogenous vehicle to transport the porphyrin compound to the target tissues (U.S. Pat. No. 5,214,036). It is known that hydrophobic or amphipathic drugs encapsulated in liposomes have the tendency to release from the liposome in the presence of blood or blood components (Wasen, K. M. et al. (1993) *Antimicrob. Agent Chemother.* 37, 246-250). Depending upon the chemical nature of the drug, the released drug may remain in free form in the blood circulation or incorporate into the surrounding plasma lipoproteins and proteins. Due to dilution and distribution into the body pool as well as elimination by renal filtration, the amounts of drug that can be delivered to the target tissues, particularly to the eye tissues with a free drug formulation or an unstable leaky liposome formulation are extremely limited.

BRIEF SUMMARY OF THE INVENTION

It is one object of the present invention to provide a liposome composition for delivering high pay-load of a therapeutic agent to neovascularization sites of the eyes in a patient in need thereof. The liposome composition of the invention comprises a particle forming component composed of a variety of vesicle-forming lipids, and an agent-carrying component able to form a complex with the therapeutic agent via electrostatic charge-charge interaction or hydrophobic-hydrophobic interaction. The vesicle-forming lipids are selected from a group of amphipathic lipids having hydrophobic and polar head group moieties alone or in combination; and the agent-carrying component comprises a chemical entity that contains one or more negatively or positively charged groups. The therapeutic agent is entrapped in the liposome composition and the liposome composition comprising the therapeutic agent has a mean particle diameter of about 30 to 200 nm and can accumulate at the neovascularization sites of the eyes 24 hours after the intravenous administration of the liposome composition comprising the therapeutic agent to the patient.

It is another object of the present invention to provide a method of delivering high pay-load of a therapeutic agent to neovascularization sites of the eyes of a patient in need thereof, comprising systemically administering said therapeutic agent in the liposome composition of the invention to said patient.

Additional features and advantages of the present invention will be set forth in part in the description which follows, and in part will be obvious from the description, or may be learned by practice of the invention. The features and advantages of the invention will be realized and attained by means of the elements and combinations as described.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIGS. 4A through to 4C are single-photon emission computed tomography (SPECT) images of rats taken at 3, 24, and 48 hours after the intravenous administration of $In^{111}$-encapsulated liposome to unilateral CNV-rats.

DETAILED DESCRIPTION OF THE INVENTION

For a better understanding of the present invention, some of the terms used herein are explained in more detail.

"Derivatize" is a term used to describe a conversion of a chemical compound into a derivative. Therefore, "a vesicle-forming lipid derivatized with a hydrophilic polymer" means the lipid is converted into a lipid derivative by adding a hydrophilic polymer thereto.

The term "neovascularization" as used herein refers to abnormal growth of blood vessels in areas of the eye including the inner back lining where images are processed (retina), the clear front covering of the eyeball (cornea) and even from the choroid through a break in the Bruch membrane into the sub-retinal pigment epithelium (sub-RPE) or subretinal space.

The present invention provides the present invention to provide a liposome composition for delivering high pay-load of a therapeutic agent to neovascularization sites of the eyes in a patient in need thereof. According to the invention, the liposome composition is a micro-size or nano-size particle which comprises a particle-forming component and an agent-carrying component. The micro-size particle has a mean particle diameter between 100 to 200 nm, and preferably between 100 to 150 nm. The nano-size particle has a mean particle diameter ranging between 30 to 100 nm, and preferably between 50 to 100 nm. The particle-forming component forms an enclosed lipid barrier of the particle. The agent-carrying component interacts with a therapeutic agent either by electrostatic charge-charge interaction or hydrophobic-hydrophobic interaction to forms a stable complex. The stable complex prevents or minimizes the release of the therapeutic agent from the carrier particle in blood circulation and allows high pay-load of the agent to be delivered to target tissues, including the neovascularization sites of the eye.

According to an embodiment of the invention, the liposome composition comprising the therapeutic agent is systemically administered to the patient in need thereof. In a preferred embodiment of the invention, the liposome composition comprising the therapeutic agent was intravenously administered to the patient, and then the therapeutic agent (entrapped in the liposome composition) accumulated at the neovascularization sites of the eyes 24 hours after the administration.

In accordance with embodiments of the invention, the neovascularization sites include choroidal neovascularization lesions and retinal neovascularization lesions of the eyes.

Detailed descriptions of the particle-forming component and agent-carrying component for preparing the liposome composition are given below:

Particle-Forming Component

The particle-forming component described in the present invention is composed of a variety of vesicle-forming lipids, including any amphipathic lipids having hydrophobic and polar head group moieties, such as phospholipids, diglycerides, dialiphatic glycolipids, sphingomyelin, glycosphingolipid, cholesterol and derivatives thereof, alone or in combinations.

The preferred vesicle-forming lipids are those having two hydrocarbon chains, typically acyl chains, and a polar head group. For example, the phospholipids such as phosphatidic acid (PA), phosphatidylcholine (PC), phosphatidylglycerol (PG), phosphatidylethanolamine (PE), phosphatidylinositol (PI), phosphatidylserine (PS) and sphingomyelin (SM) have two hydrocarbon chains ranging from about 12-22 carbon atoms in length, and with varying degree of unsaturation. Preferably, the vesicle-forming lipid is a phospholipid having a long carbon chain of (—CH2)n, and n is at least 14. These phospholipids may be naturally occurring or synthetic. And the naturally occurring phospholipids may be modified by subjecting to various degrees of hydrogenation.

The particle-forming component may contain a hydrophilic polymer that has a long chain highly hydrated flexible neutral polymers attached to lipid molecules. Examples of the hydrophilic polymer include, but are not limited to polyethylene glycol (PEG), polyethylene glycol derivatized with Tween, polyethylene glycol derivatized with distearoylphosphatidylethanolamine (PEG-DSPE), ganglioside $GM_1$, and synthetic polymers. In accordance with one embodiment of the invention, the hydrophilic polymer is PEG having a molecular weight between 500 to 5000 daltons. In one preferred embodiment, PEG has a molecular weight of approximately 2000. It has been reported that PEG-PE incorporation in liposomes produces steric stabilization resulting in longer circulation times in blood (Allen, T. M. et al. (1991) *Biochim. Biophys. Acta* 1066, 29-36; Papahadjopoulos, D. et al. (1991) *Proc. Natl. Acad. Sci. USA*. 88, 11460-11464).

In addition, the particle-forming component may include a lipid-conjugate of an antibody or a peptide, which acts as a targeting moiety enabling the micro- or nano-particle to specifically bind a target cell bearing the target molecule (cell surface marker) to which the antibody or peptide is directed. The cell surface markers include, but are not limited to platelet-derived growth factor (PDGF), epidermal growth factor (EGF), vascular endothelial growth factor (VEGF), insulin-like growth factor (IGF), transforming growth factor B (TGF-B), fibroblast growth factor (FGF), interleukin 2 (IL-2), interleukin 3 (IL-3), interleukin 4 (IL-4), interleukin 1 (IL-1), interleukin 6 (IL-6), interleukin 7 (IL-7) and nerve growth factor (NGF).

Agent-Carrying Component

As described above, the agent-carrying component has the ability to form a complex with a therapeutic agent either via electrostatic charge-charge interaction or hydrophobic-hydrophobic interaction. The agent-carrying component can be any suitable chemical entity that contains one or more negatively or positively charged groups. The chemical entity may be charged by deprotonation to a negative charged agent-carrying component or by protonation to a positive charged agent-carrying component.

The negatively charged agent-carrying component may be a divalent anion, a trivalent anion, a polyvalent anion, a polymeric polyvalent anion, a polyanionized polyol, or a polyanionized sugar. Examples of the divalent and trivalent anions include, but are not limited to sulfate, phosphate, pyrophosphate, tartrate, succinate, maleate, borate, and citrate. The polyanionic polymer has an organic or inorganic backbone, and a plurality of anionic functional groups. Examples of the polyanionic polymers include but are not limited to polyphosphate, polyvinylsulfate, polyvinylsulfonate, polycarbonate, acidic polyaminoacids and polynucleotides.

The positively charged agent-carrying component, described in the present invention, can be any organic polycationics such as polyamines, polyammonium molecules, and basic polyamino acids. A preferred polyamine includes spermidine and spermine. Small polycationic molecules are known to condense nucleic acids via electrostatic charge-charge interactions (Plum, G. E. et al. (1990) *Biopolymers* 30, 631-643). The positively charged agent-carrying component can also be amphiphilic cationic lipids that carry a net positive charge at physiological pH. Such lipids include, but are not limited to dioleoyldimethylammonium chloride (DODAC), N-[2,3-(dioleyloxy)propyl]-N,N,N-trimethylammonium chloride (DOTMA), Dimethyldioctadecylammonium Bromide (DDAB), 1,2-Dioleoyl-3-Trimethylammonium-Propane (DOTAP), 3β-[N-(N',N'-Dimethylaminoethane)-carbamoyl]Cholesterol Hydrochloride (DC-Chol) and 1,2-dimyristyloxypropyl-3-dimethyl-hydroxy ethyl ammonium bromide (DMRIE). The amphiphilic cationic lipids may participate or assist the particle-forming component to form a surrounding lipid barrier of the particle.

In addition, the agent-carrying component can be a chelating agent that forms chelating complex with a divalent or trivalent cation, including a transition metal, such as nickel, indium, iron, cobalt, calcium, magnesium ions. Examples of the chelating agents include, but are not limited to thylenediaminetetraacetic acid (EDTA), diethylenetriaminepentaacetic acid (DTPA), nitroltriacetic acid (NTA), deferoxamine, and dexrazoxane.

The agent-carrying component can also be a cyclodextrin. Cyclodextrin is a cyclic oligosaccharide with lipophilic inner cavity and hydrophilic outer surface capable of forming non-covalent inclusion complexes with a large variety of therapeutic agents with poor water solubility. Examples of the cyclodextrins include, but are not limited to α-cyclodextrin, β-cyclodextrin, γ-cyclodextrin, hydroxyethyl-β-cyclodextrin, hydroxypropyl-β-cyclodextrin, methyl-β-cyclodextrin, dimethyl-β-cyclodextrin, randomly dimethylated-β-cyclodextrin, randomly methylated-β-cyclodextrin, carboxymethyl-β-cyclodextrin, carboxymethyl ethyl-β-cyclodextrin, diethyl-β-cyclodextrin, tri-O-methyl-β-cyclodextrin, tri-O-ethyl-β-cyclodextrin, tri-O-butyryl-α-cyclodextrin, tri-O-valeryl-β-cyclodextrin, di-O-hexanoyl-β-cyclodextrin, glucosyl-β-cyclodextrin, and maltosyl-β-cyclodextrin.

Accordingly, the liposome composition of the present invention has therapeutic agent and the agent-carrying component entrapped in the particle-forming component as shown in FIG. 1B. Therefore, the liposome composition stably encapsulates the water-soluble therapeutic agent, so that less than 10% of the therapeutic agent is separated from the particle-forming component in the blood plasma after one hour of incubation at 37° C. Also, the liposome composition stably intercalates water-insoluble therapeutic agent, so that less than 10% of the therapeutic agent is separated from the particle-forming component in the blood plasma after one hour of incubation at 37° C.

And while the present embodiment provided systemic delivery of high pay-load of the therapeutic agent to several neovascularization sites of the eye, particularly pathological neovascularization sites associated with diseases such as age-related macular degeneration, choroidal neovascularization, macular edema, diabetic retinopathy, or glaucoma, it is understood by one having ordinary skill in the art that delivery of high pay-load of the therapeutic agent to other neovascularization sites may be achieved by the system described in the present invention.

It should be noted that the therapeutic agent applicable in the present invention may include an angiostatic steroid or an inhibitor for protein kinase C, vascular endothelial growth factor receptor kinase, platelet-derived growth factor receptor kinase, aldose reductase, matrix metalloproteinase, or urokinase. And the therapeutic agent may also include a nucleic acid-like component such as therapeutic DNA, RNA, siRNA or antisense oligonucleotide.

The following examples illustrate the method of delivering high pay-load of a therapeutic agent via blood stream to the neovascularization sites of the eye. The examples are in no way intended to limit the scope of the present invention.

EXAMPLE 1:

Fluorescein Angiography (FAG) of Fluorescein-Labeled Liposomes in Experimental Choroidal Neovascularization (CNV) in Rats Induction of Unilateral-CNV in Rats Brown Norway (BN) pigmented rats, weighing between 200 and 250 gram, were anesthetized with intramuscular injection of 0.15 ml/kg of an equal-volume mixture of 2% lidocaine (Xylocalne; Astra, Astra Södertalje, Sweden) and 50 mg/mL ketamine (Ketalar; Parke-Davis, Morris Plains, N.J.). After anesthetizing, the right pupils were dilated with 1% tropicamide (1% Mydriacyl; Alcon Laboratories, Watford, UK). A small piece of transparent sheet (3M, Minneapolis, Minn.) approximately 3 mm in diameter was attached to the cornea by sodium hyaluronidase (Healon; Pharmacia and Upjohn, Inc., Kalamazoo, Mich.) to serve as a contact lens. Krypton laser (Novus Omni; Coherent, Palo Alto, Calif.) irradiation was delivered through a slit lamp (Carl Zeiss, Oberkochen, Germany). Laser parameters used were as follows: spot size of 100 mm, power of 120 to 160 mW, and exposure duration of 0.1 second. An attempt was made to break Bruch's membrane, as clinically evidenced by central bubble formation, with or without intra-retinal or choroidal hemorrhage. Four lesions were created between the major retinal vessels in right fundus. CNV was evaluated on day 14 by opthalmoscopy, fundus photography, and conventional fluorescein angiography (FAG) modified from (DiLoreto D, Grover D A, Del Cerro C. (1994) *Curr Eye Res.* 13, 157-61). The animals were handled in accordance with the Association for Research in Vision and Opthalmology (ARVO) Statement for the Use of Animals in Ophthalmic and Vision Research.

Figure 2:
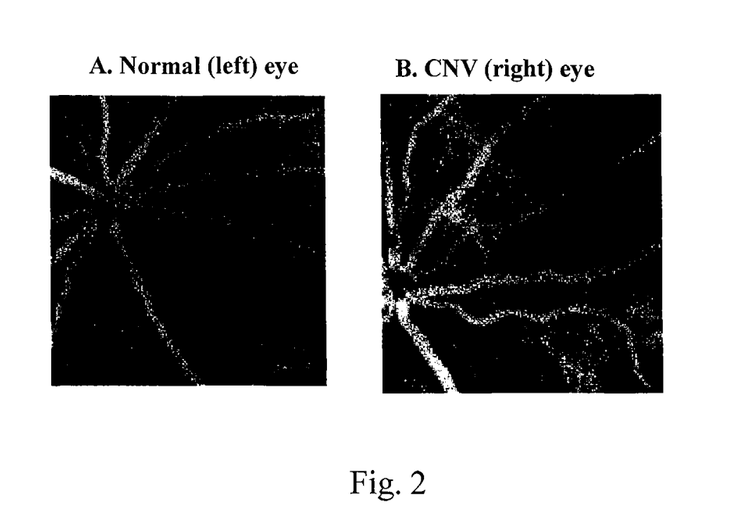
FIGS. 2A and 2B are fluorescein angiograms illustrating a normal (left) eye and an (right) eye with choroidal neovascularization (CNV) lesions in an unilateral CNV-rat.

Fluorescein sodium (10%; 0.1 ml/kg; Fluorescite™; Alcon, Fort Worth, Tex.) was injected through the tail vein of the anesthetized rats 14 days after laser photocoagulation. The CNV lesions were recorded with a digital fundus camera (Retinal Angiography; Heidelberg Engineering, Heidelberg, Germany). Late-phase angiograms were obtained 8 minutes after injection, and digital fundus pictures of bilateral eyes were taken within 1 minute. FIG. 2 shows the FAG of the normal (A) and CNV (B) eyes on day 14 post photocoagulation. Fluorescien leakage spots were observed near the lesion sites in all laser treated eyes in comparison with the intact retinal vessels seen in the normal eye.

Material

Lipid raw materials, distearoylphosphatidylcholine (DSPC), cholesterol, and 1,2-Distearoyl-sn-Glycerol-3-Phosphoethanolamine-N-methoxy-(polyethylene glycol)-2000 ($MPEG_{2000}$-DSPE) were obtained from NOF Corp. (Tokyo, Japan). N-(methoxy-(polyethylene glycol)-oxycarbonyl)-DSPE was purchased from Avanti Polar Lipids (Alabaster, Ala.).

Preparation of Fluorescein-Encapsulated Liposome

A lipid mixture of DSPC, cholesterol, and $MPEG_{2000}$-DSPE (molar ratio 60:40:6) was dissolved in chloroform and then evaporated to dryness under vacuum by a rotary evaporator. The lipid film was re-suspended in 10% fluorescein sodium solution (Fluorescite™; Alcon, Fort Worth, Tex.) at 62° C. to 65° C. to form a lipid suspension. The resulting lipid suspension was frozen and thawed 7 times, and followed by repeated extrusion under argon 10 times through polycarbonate filters (Corning Nucleopore, Wash., USA) of 200 nm pore size and then 10 times through filters of 100 nm pore size using a pressure extruder (Lipex Biomembranes Inc., Vancouver, Canada) at 62° C. to 65° C. The final lipid concentration of the liposome was 15 µmol/mL and the mean particle diameter of the liposome was 99.3 (99.3±20) nm as determined by a dynamic laser particle sizer (N4+; Coulter Electronics, Hialeah, Fla., USA) and characterized below.

| parameter | fluorescein-encapsulated liposome |
|---|---|
| total lipid concentration | 15 µmol/mL |
| mean particle diameter | 99.3 ± 20 nm |

Preparation of Fluorescein-Labeled Liposome

A lipid mixture of DSPC, cholesterol, $MPEG_{2000}$-DSPE and N-(methoxy-(polyethylene glycol)-oxycarbonyl)-DSPE, a fluorescein-labeled lipid, (molar ratio 60:40:6:0.5) was dissolved in chloroform and then evaporated to dryness under vacuum by a rotary evaporator. The lipid film was re-suspended in 0.9% NaCl at 62° C. to 65° C. to form a lipid suspension. The resulting lipid suspension was frozen and thawed 7 times, followed by repeated extrusion under argon 10 times through polycarbonate filters (Corning Nucleopore, Wash., USA) of 200 nm pore size and then 10 times through filters of 100 nm pore size using a pressure extruder (Lipex Biomembranes, Inc., Vancouver, Canada) at 62° C. to 65° C. The final lipid concentration of the liposome was 64 µmol/mL and the mean particle diameter of the liposome was 99.6 (99.6±29.8) nm as determined by a dynamic laser particle sizer characterized below.

| parameter | fluorescein-labeled liposome |
|---|---|
| total lipid concentration | 64 µmol/mL |
| mean particle diameter | 99.6 ± 29.8 nm |

In Vivo Study

Since FAG is widely applied for studying CNV, the in vivo study was conducted to demonstrate the presence of fluorescein-labeled liposome in CNV sites using the FAG technique. A fluorescein-encapsulated liposome was tested initially. However, the encapsulated fluorescein sodium diffused and released rapidly from the liposome in blood stream and extreme weak fluorescein angiograms were observed for the rats receiving the fluorescein-encapsulated liposome (data not shown). On the other hand, a fluorescein-labeled lipid that could be intercalated into the lipid bilayer was used in the subsequent experiment. And the fluorescence-labeled liposome exhibited a circulation half-life ($t_{1/2}$) of about 10 hours in BALB/c mice.

Four unilateral-CNV rats were used in this study. One rat was injected intravenously with 0.1 mL of fluorescein sodium and served as a control. The three remaining rats were administered with 0.95 mL of fluorescein-labeled liposome. FAG was performed at various time points as indicated in table I below.

TABLE I

| Rat No. | Treatment | FAG |
|---|---|---|
| 1 | Fluorescein sodium (0.1 mL) | 24 h after the i.v. injection |
| 2 | Fluorescein-labeled liposome (0.95 mL) | Immediate after the i.v. injection |
| 3 | Fluorescein-labeled liposome (0.95 mL) | 3 h after the i.v. injection |
| 4 | Fluorescein-labeled liposome (0.95 mL) | 24 h after the i.v. injection |

Figure 3:
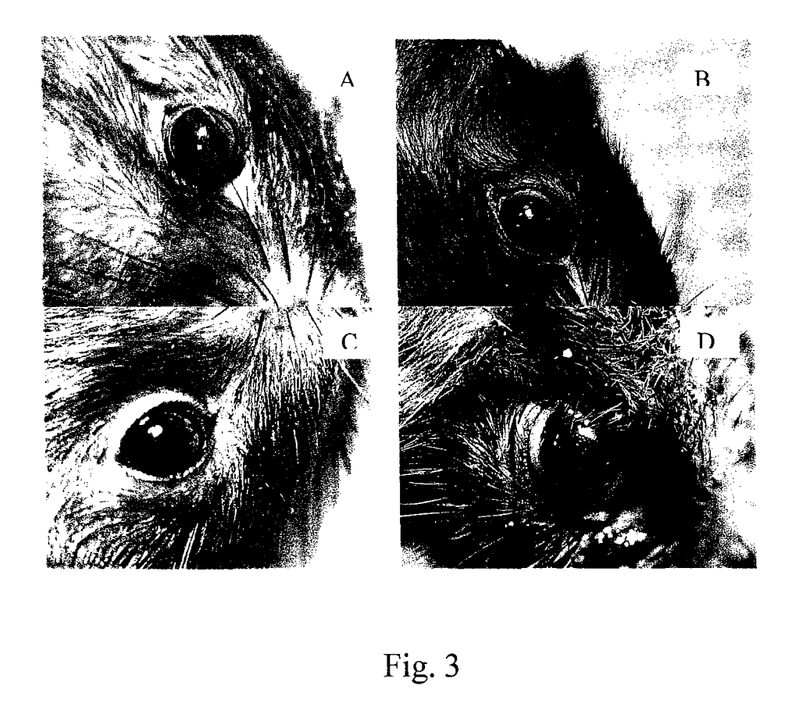
FIGS. 3A through 3D show visual appearance of rat eyes at various times after the intravenous administration of fluorescein sodium (F) or fluorescein-labeled liposome (FL) to unilateral CNV-rats.

The fluorescein angiograms obtained with fluorescein-labeled liposome were still unsatisfactory even shortly (about 5 minutes) after the liposome administration (data not shown). FIG. 3C shows that the rat eye looks normal immediately after the fluorescein-labeled liposome was administered. Nevertheless, visual observation showed that both normal and the CNV eyes slowly turned to milky-green and remained in this color 24 hours after the liposome administration (FIG. 3D). This was in contrast with the control rat that received fluorescein sodium (FIGS. 3A and 3B), where the eyes of the control rat turned to greenish color immediately following the fluorescein administration and the greenish color quickly disappeared within an hour. Thus, the result suggested that the fluorescein-labeled liposome with a stably intercalated fluorescein-labeled lipid could reach the eye and retain in the region for a sustained period of time than the free fluorescein sodium.

EXAMPLE 2

Accumulation of $In^{111}$-Encapsulated Liposome in Neovascularization Sites of the Eye Unilateral-CNV Model The same unilateral-CNV model in rats described in example 1 was used, except twenty lesions were created between the major retinal vessels in right fundus by laser photocoagulation. In the process of monitoring the behavior of these animals, 2 to 3 out of the 10 rats were unable to walk straight. This abnormal behavior might be related to vision loss of the right eye as the result of laser photocoagulation. There were no other noticeable side effects observed in these rats.

Preparation of $In^{111}$-DTPA and $In^{111}$-Encapsulated Liposome $In^{111}$-DTPA was prepared by mixing 500 mCi of $In^{111}$ $Cl_3$ (PerkinElmer, Mass., USA) with 20 μL of DTPA (deithylenetriamine pentaacetic acid, 5 mg/mL in water) and incubated at 50° C. for 15 minutes. The $In^{111}$-oxaine used to prepare $In^{111}$-encapsulated liposome was prepared by mixing about 2 mCi of $In^{111}$ $Cl_3$ in 0.2 M sodium acetate, pH 5.5 with 100 μg of oxine (Sigma-Aldrich, Shanghai, China) in ethanol. After 15 minutes incubation at 50° C., the lipophilic product was extracted with chloroform.

To prepare $In^{111}$-encapsulated liposome, the lipid mixture containing DSPC, cholesterol, and PEG2000-DSPE (molar ratio 3:2:0.3) was dissolved in 0.5 mL of ethanol. The dissolved lipid in ethanol was injected into 1.67 mL of 5 mM DTPA solution at 62° C. to 65° C. The resulting lipid suspension was extruded under argon 10 times through polycarbonate filters (Corning Nucleopore, Wash., USA) of 200 nm pore size and then 10 times through filters of 100 nm pore size by a pressure extruder (Lipex Biomembranes, Inc., Vancouver, Canada) at 62° C. to 65° C. The external DTPA solution was exchanged with 0.9% sodium chloride by a Sephadex G50-column. The $In^{111}$ was loaded into liposome by incubating $In^{111}$-oxine with DTPA-liposome at 60° C. for 30 minutes and the non-encapsulated $In^{111}$ was removed by Sephadex G50 gel filtration. The mean particle diameter of the $In^{111}$-encapsulated liposome was 99.2 (99.2±26.3) nm as determined by a dynamic laser particle sizer and characterized below.

| parameter | $In^{111}$-encapsulated liposome |
|---|---|
| total lipid concentration | 15 μmol/mL |
| total DTPA concentration | 5 μmol/mL |
| DTPA:lipid ratio | 0.33 |
| mean particle diameter | 99.2 ± 26.3 nm |

Single-Photon Emission Computed Tomography (SPECT) Imaging

The SPECT imaging was carried out at 3, 24, and 48 hours after the injection of 250 μCi of either $In^{111}$-DTPA or $In^{111}$ encapsulated liposome. At indicated time, each rat was anesthetized with intramuscular injection of 0.15 ml/kg of phenobarbital and SPECT imaging was performed on an e.cam Multiangle Cardiac™ image system (Siemens, Munich, Germany) equipped with a pinhole collimator. The center field of view was 25.4 $cm^2$ and a single energy centered window was used at 159 keV, with a width of 20%. A sequence of scans (22 min/frame×6) was obtained over a period of 15 min. Images were reconstructed in a 128×128 (pixels) format from data with 32 projections distributed over 180° around the rat and a 40 s scan for each projection. The projections of each experiment were processed by reconstruction using filtered back projection, with a low-pass Butterworth filter of order 22.4 and cutoff frequency of 0.43. Each transverse image was reconstructed in a 128×128 array with a pixel size of 1.9×1.9 mm and a zoom of 2.0×.

Bio-Distribution of $In^{111}$-DTPA and $In^{111}$-Encapsulated Liposome

After the SPECT, all rats were sacrificed and perfused with normal saline containing 2 mM EDTA. Animals were dissected to isolate both normal (left) and CNV (right) eyes. The isolated eyes were weighted and radioactivity associated with the eyes was counted by a γ scintillation counter (Cobra II Autogamma, Packed, USA). The uptake of radiotracer in the eyes or other tissues was expressed in counts per minute (cpm) with decay correction and was normalized as percent of injection dose per gram tissue (% ID/g).

In Vivo Study

The experiment determines the biodistribution of $In^{111}$, a small molecular marker and $In^{111}$-encapsulated liposome, a lipid nano-particle in an experimental CNV model. Ten unilateral CNV rats were randomly divided into two groups with 4 and 6 rats, respectively. Group 1 received 250 μCi of $In^{111}$-DTPA and group 2 received 250 μCi of $In^{111}$-encapsulated liposome by intravenous injection. The basic design of the experiment is listed in table II below.

TABLE II

| Group | Treatment | Dose level | SPECT time[1] | Number of animal |
|---|---|---|---|---|
| 1 | $In^{111}$-DTPA | 250 μCi | 3 and 24 hours | 2 |
|  |  |  | 3 and 48 hours | 2 |
| 2 | $In^{111}$-encapsulated liposome | 250 μCi | 3 and 24 hours | 3 |
|  |  |  | 3 and 48 hours | 3 |

[1]The SPECT image was performed at either 3 and 24 or 3 and 48 hours after the intravenous administration. After the SPEC, all animals were sacrificed, perfused and then dissected. Eyes were isolated and radioactivity associated with the eyes was counted.

Figure 4:
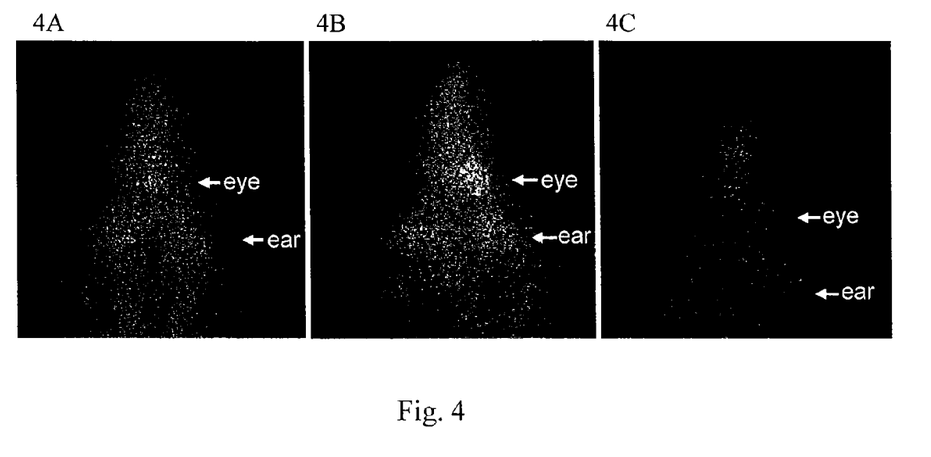
Figure 5:
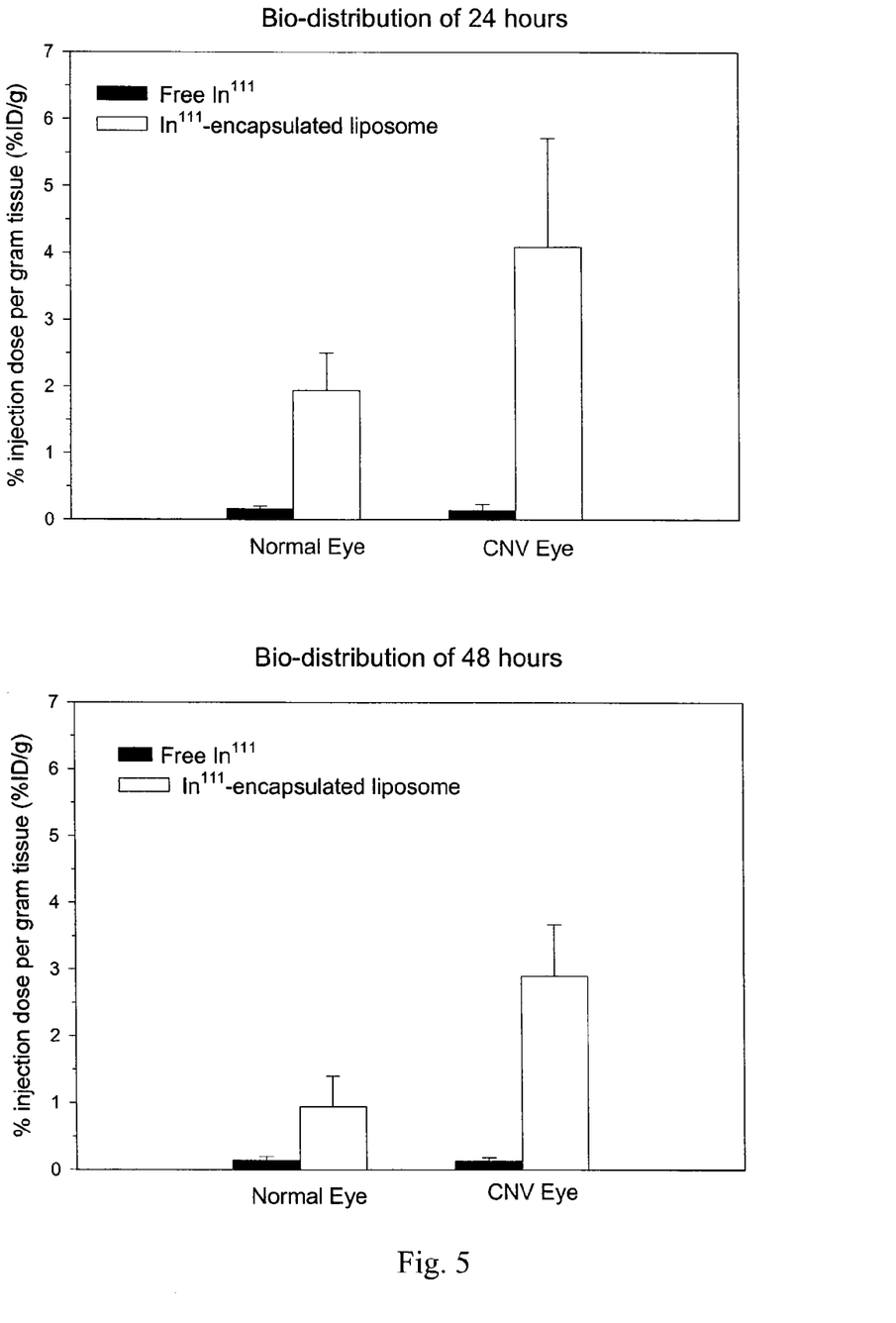
FIG. 5 shows the biodistribution of radioactivity at various times in normal and CNV-eyes in unilateral CNV-rats received with either $In^{111}$-DPTA (Free $In^{111}$) or $In^{111}$-encapsulated liposome.

The SPECT images of rats having received $In^{111}$-DTPA did not show any $In^{111}$ accumulation in both normal and CNV eyes even at 3 hours after the dosing (data not shown). In contrast, SPECT images of the animals that received $In^{111}$-encapsulated liposome clearly demonstrated the accumulation of radioactivity in both eyes even at 48 hours after the liposome injection. Referring to FIGS. 4A through to 4C, stronger radiation activity was seen in the CNV eyes than that in the normal eyes at 3 hours post injection (FIG. 4A), and the difference between the two eyes was maximal at 24 hours post injection (FIG. 4B). The SPECT images were less obvious after 48 hours of the liposome dosing (FIG. 4C).

Table III below shows the specific radioactivity (% ID/g) distributed in the normal and CNV eyes of rats following the intravenous administration of either $In^{111}$-DTPA or $In^{111}$-encapsulated liposome. For rats that received the $In^{111}$-DTPA, low levels of the $In^{111}$, ranging from 0.13±0.05 to 0.16±0.04 (% ID/g), were detected in both eyes at 24 and 48 hours post-injection, respectively. There was no difference in specific radioactivity between the normal and CNV eyes. However, rats having received $In^{111}$-encapsulated liposome showed a significantly greater radioactivity in the CNV eyes than in the normal eyes at 24 and 48 hours post-injection. The specific radioactivity detected from the CNV eyes was 4.1±1.6 and 2.9±0.8% ID/g at 24 and 48 hours, respectively, and 1.9±0.6 and 0.9±0.5% ID/g at 24 and 48 hours, respectively for the normal eye. Accordingly, the data showed that the $In^{111}$-encapsulated liposome was able to deliver 22- and 29-fold greater $In^{111}$ to the CNV eyes than the $In^{111}$-DTPA at 24 and 48 hours post injection, respectively.

TABLE III

| Post injection time | Subject | | | |
|---|---|---|---|---|
| | $In^{111}$-encapsulated liposome | | $In^{111}$-DTPA | |
| | Normal eye | CNV eye | Normal eye | CNV eye |
| 24 hours | 1.94 ± 0.56 | 4.09 ± 1.63 | 0.16 ± 0.04 | 0.14 ± 0.09 |
| 48 hours | 0.94 ± 0.46 | 2.90 ± 0.77 | 0.14 ± 0.06 | 0.13 ± 0.05 |

[1]The unit of data is the percent of injection dose per gram tissue (% ID/g).
[2]Numbers are means ± s.d.

It should be noted from SPECT imaging of rats received with $In^{111}$-encapsulated liposome that there was no distinguishable difference between the normal and CNV eyes after 48 hours (FIG. 4C), but remarkable difference was obtained in the bio-distribution study as evidenced in Table III. In analyzing all the data, it was found that the radioactivity presented in the blood pool was higher than that accumulated in the eyes at 48 hours post injection. The high background radioactivity may explain why there was no difference in SPECT imaging but showed significant difference between the two eyes after the perfusion.

The data strongly support the hypothesis that the systemic injected micro- or nano-particle, such as liposome can reach the back of the eye and accumulate in the neovascularization sites of the eye. Since large drug payload can be carried in liposome composition described in the present invention, the liposome can effectively deliver a therapeutic dose of the drug to treat the eye diseases including AMD and RD that occur at the back of the eye.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We Claim:

1. A method of delivering high pay-load of a therapeutic agent for an eye disease to neovascularization sites of the eyes of a patient, comprising:
   systemically administering a liposome composition to said patient by intravenous injection;
   wherein the liposome composition has a mean particle diameter of about 30 to 200 nm comprising a particle-forming component composed of vesicle-forming lipids selected from the group consisting of amphipathic lipids having hydrophobic and polar head group moieties alone or in combination, and an agent-carrying component that contains one or more negatively or positively charged groups, wherein said agent-carrying component forms a stable, soluble salt with the therapeutic agent via electrostatic charge-charge interaction so as to prevent or minimize the release of the therapeutic agent to blood circulation and allow the therapeutic agent to be delivered to and accumulate at the neovascularization sites at the back of the eyes 24 hours after the systemic administration of the liposome composition to the patient, and wherein the liposome lacks a targeting moiety for a cell surface marker.

2. The method according to claim 1, wherein the liposome composition is a micro-sized particle having a mean particle diameter between 100 to 200 nm.

3. The method according to claim 2, wherein the liposome composition is a micro-sized particle having a mean particle diameter between 100 to 150 nm.

4. The method according to claim 1, wherein the liposome composition is a nano-sized particle having a mean particle diameter between 30 to 100 nm.

5. The method according to claim 4, wherein the liposome composition is a nano-sized particle having a mean particle diameter between 50 to 100 nm.

6. The method according to claim 1, wherein the vesicle-forming lipid is a phospholipid having a long carbon chain of $(-CH_2)n$, and n is at least 14.

7. The method according to claim 1, wherein the amphipathic lipids are selected from the group consisting of phospholipids, diglycerides, dialiphatic glycolipids, sphingomelin, glycosphingolipid, cholesterol and derivatives thereof, alone or in combinations.

8. The method according to claim 7, wherein the phospholipids are selected from the group consisting of phosphatidic acid (PA), phosphatidyl choline (PC), phosphatidyl glycerol (PG), phosphatidyl ethanolamine (PE), phosphatidylinositol (PI), phosphatidylserine (PS) and sphingomyelin (SM).

9. The method according to claim 8, wherein the phospholipids are selected from the group consisting of phosphatidyl choline (PC), phosphatidyl glycerol (PG), and phosphatidyl ethanolamine (PE).

10. The method according to claim 9, wherein the phospholipid is selected from the group consisting of egg phosphatidyl choline (EPC), hydrogenated egg phosphatidyl choline (HEPC), soy phosphatidyl choline (SPC), hydrogenated soy phosphatidyl choline (HSPC), dipalmitoyl phosphatidyl choline (DPPC) and distearyloyl phosphatidyl choline (DSPC), diarachidoyl phosphatidyl choline, dimyristoyl phosphatidyl ethanolamine (DMPE), dipalmitoyl phosphatidyl ethanolamine (DPPE), distearoyl phosphatidyl ethanolamine (DSPE), diarachidoyl phosphatidyl ethanolamine (DAPE), and dipalmitoyl phosphatidyl glycerol (DPPG).

11. The method according to claim 1, wherein the agent-carrying component is a negatively charged agent-carrying component, selected from the group consisting of a divalent anion, a trivalent anion, a polyvalent anion, a polymeric polyvalent anion, a polyanionized polymer.

12. The method according to claim 11, wherein the polyanionized polymer is a polyanionized polyol or a polyanionized sugar.

13. The method according to claim 11, wherein the polyanionized polymer is polyphosphate, polyvinylsulfate, polyvinylsulfonate, polycarbonate, acid polyaminoacid or polynucleotide.

14. The method according to claim 1, wherein the neovascularization sites include choroidal neovascularization lesions and retinal neovascularization lesions.

* * * * *